United States Patent [19]

Ackmann et al.

[11] Patent Number: 4,966,623

[45] Date of Patent: Oct. 30, 1990

[54] USE OF GAMETOCIDAL PYRAZOLES TO PRODUCE HYBRID SEED

[76] Inventors: Stephen A. Ackmann, 3296 W. 33rd St., Indianapolis, Ind. 46222; James R. Beck, 10023 Penrith Dr., Indianapolis, Ind. 46229; Fred L. Wright, 124 Lakeview Ct. North, Greenfield, Ind. 46140

[21] Appl. No.: 405,786

[22] Filed: Sep. 11, 1989

Related U.S. Application Data

[60] Division of Ser. No. 271,127, Nov. 14, 1988, which is a division of Ser. No. 145,735, Jan. 15, 1988, Pat. No. 4,801,326, which is a continuation of Ser. No. 13,520, Feb. 11, 1987, abandoned, which is a continuation-in-part of Ser. No. 947,139, Dec. 29, 1986, abandoned, which is a continuation of Ser. No. 841,405, Mar. 19, 1986, abandoned.

[51] Int. Cl.$^5$ .............................................. A01N 33/56
[52] U.S. Cl. ................................................................ 71/92
[58] Field of Search ........................................... 71/92

[56] References Cited

U.S. PATENT DOCUMENTS 4,666,504  5/1987  Beck et al. ............................. 71/92
4,775,409 10/1988  Beck ....................................... 71/92

Primary Examiner—Robert W. Ramsuer

[57] ABSTRACT

Use of a 4,5-dicarboxy or 5-carboxamido-4-carboxy (or derivatized carboxy)-1-(3,5-disubstituted-phenyl)-pyrazole in the production of hybrid seed, and a method for producing 5-carboxamido-4-carboxy-1-(3,5-dimethylphenyl)pyrazole.

3 Claims, No Drawings

USE OF GAMETOCIDAL PYRAZOLES TO PRODUCE HYBRID SEED

CROSS-REFERENCE

This application is a division of application Ser. No. 07/271,127, filed 11/14/88 which is a division of application Ser. No. 07/145,735, filed Jan. 15, 1988, now U.S. Pat. No. 4,801,326, which is a continuation of Ser. No. 07/013,520, filed Feb. 11, 1987, now abandoned, which is a C-I-P of Ser. No. 06/947,139, filed Dec. 29, 1986, now abandoned, which is a continuation of Ser. No. 06/841,405, filed Mar. 19, 1986, now abandoned.

FIELD OF THE INVENTION

This invention belongs to the fields of plant hybridization and organic chemistry, particularly, agricultural chemistry. Very important improvements in the hardiness and yield of cultivated plants, particularly grains, have been made by the technique of hybridization. In the past, hybridizing those species, in which each plant produces both pollen and pollen-receiving organs, has been very difficult.

Compounds have been found which are capable of inhibiting formation of pollen. The use of such a compound greatly simplifies hybridization. Plants of the two strains to be crossed are simply planted adjacent to one another, as in long, relatively narrow plots, and the plots of one of the strains are treated with a pollen formation inhibitor. All of the seed produced by the treated plants will be hybrid seed, originating from pollen contributed by the untreated plants, if the pollen formation inhibitor is perfectly effective.

Compounds having pollen formation inhibiting activity have been taught in the past by Fujimoto, U.S. Pat. No. 4,345,934, by McNulty and Warner, U.S. Pat. No. 4,147,528, and by Carlson, U.S. Pat. No. 4,238,220.

SUMMARY OF THE INVENTION

This invention provides a series of pollen formation inhibiting pyrazoles of the formula

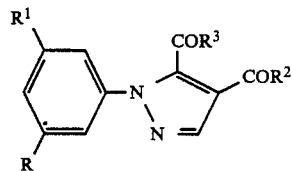

(1)

wherein
R and $R^1$ independently represent chloro, bromo or methyl;
$R^2$ is hydroxy, $C_1-C_4$ alkoxy, $C_3-C_4$ alkenoxy, $C_3-C_4$ alkynoxy, or a phytologically-acceptable moiety forming a salt of the carboxylic acid;
$R^3$ is $NH_2$ hydroxy, or a phytologically-acceptable moiety forming a salt of the carboxylic acid; or $R^2$ and $R^3$ combine to form an imide;
provided that $R^3$ is $NH_2$ when $R^2$ is alkoxy, alkenoxy or alkynoxy; and that $R^2$ and $R^3$ are the same when $R^3$ is other than $NH_2$.

The invention also provides pollen formation inhibiting compositions which comprise a compound of the above formula and one or more phytologically-acceptable diluents. The invention also provides a method of inhibiting pollen formation in a cereal grain plant which is sensitive to such treatment comprising supplying to the plant at a time prior to anther formation a pollen formation inhibiting amount of a compound of the above formula.

Further, the invention provides a method of producing hybrid cereal grain seed having a male and a female parent variety, comprising planting seed of said male and female parent varieties in separate plots adjacent to each other, treating the female parent plants growing from said female parent seed with a pollen formation inhibiting method as just described, said female parent variety being sensitive to such treatment, allowing said treated female parent plants to be pollinated by the male parent plants growing from said male parent seed and to produce hybrid seed, and harvesting said hybrid seed from the treated female parent plants.

DESCRIPTION OF THE PREFERRED EMBODIMENTS

In this document, all temperatures are described in degrees Celsius. All expressions of percentage, proportion and the like are in weight units unless otherwise stated.

In the above formula, the terms $C_1-C_4$ alkoxy includes both straight-chain and branched alkyl groups such as methyl, ethyl, propyl, isopropyl, butyl, t-butyl and isobutyl linked through an oxygen atom.

The term $C_3-C_4$ alkenoxy includes such unsaturated groups as allyl and 2-methylallyl, linked through an oxygen atom. The term $C_3-C_4$ alkynoxy includes such groups as propargyl and 3-butynyl, linked through an oxygen atom.

The salts of the above formula are formed with any phytologically-acceptable moiety capable of forming a salt of the carboxylic acid. The preferred salt-forming moieties include alkali metals, amine groups, and quaternary ammonium groups. More particularly, sodium, potassium, lithium, $C_1-C_4$ alkylamino, dialkylamino and trialkylamino groups and quaternary ammonium groups wherein the nitrogen atom is substituted with four hydrogen, $C_1-C_{18}$ alkyl, phenyl or benzyl moieties are preferred. Bulky quaternary ammonium groups having one or two $C_{10}-C_{18}$ groups are more preferred.

For example, quaternary ammonium groups such as ammonium, tetramethylammonium, diethyl-dimethylammonium, diethyl-dibutylammonium, benzyltrimethylammonium, t-butyltrimethylammonium, phenyl-triethylammonium, diethyldipropylammonium, s-butyl-trimethylammonium, isobutyltriethylammonium, dimethyl-bis(tetradecyl)ammonium, trimethyl-octadecylammonium, diethyl-dodecyl-pentadecylammonium, dimethyl-decyl-heptadecylammonium and the like are useful and may be chosen for convenience in the circumstances. Further, such amines as methylamine, butylamine, triethylamine, dipropylamine and the like are convenient for salt formation.

Certain classes of the compounds of the present invention are preferred. The preferred classes are as follows. It will be understood that groups may be chosen from the preferred classes and may be combined in any desired combination to create further, more limited or more extensive preferred classes.
(1) $R^2$ is hydroxy or a salt thereof;
(2) $R^2$ is hydroxy;
(3) $R^2$ is alkoxy;
(4) $R^2$ is methoxy;
(5) $R^2$ is alkenoxy or alkynoxy;
(6) R and $R^1$ are the same;

(7) R and $R^1$ are chloro;
(8) R and $R^1$ are methyl;
(9) R and $R^1$ are chloro or bromo;
(10) $R^2$ and $R^3$ are hydroxy or a salt thereof;
(11) $R^3$ is $NH_2$.

The following compounds of the invention are mentioned to assure that the reader understands the invention.

4-carboxy-1-(3,5-dibromophenyl)-5-pyrazolecarboxamide.
1-(3-bromo-5-methylphenyl)-4-propoxycarbonyl-5-pyrazolecarboxamide.
4,5-dicarboxy-1-(3,5-dibromophenyl)pyrazole, dipotassium salt.
1-(3-chloro-5-methylphenyl)-4-isopropoxycarbonyl-5-pyrazolecarboxamide.
4-ethoxycarbonyl-1-(3,5-dimethylphenyl)-5pyrazolecarboxamide.
4-t-butoxycarbonyl-1-(3-chloro-5-methylphenyl)-5-pyrazolecarboxamide.
1-(3,5-dichlorophenyl)-4-isobutoxycarbonyl-5-pyrazolecarboxamide.
4-allyloxycarbonyl-1-(3,5-dimethylphenyl)-5-pyrazolecarboxamide.
4,5-dicarboxy-1-(3,5-dimethylphenyl)pyrazole.
4,5-dicarboxy-1-(3-bromo-5-methylphenyl)pyrazole, disodium salt.
4,5-dicarboxy-1-(3,5-dibromophenyl)pyrazole, bis(triethylamine) salt.
4-allyloxycarbonyl-1-(3,5-dichlorophenyl)-5-pyrazolecarboxamide.
1-(3,5-dichlorophenyl)-4-(2-methylallyl)oxycarbonyl-5-pyrazolecarboxamide.
4-allyloxycarbonyl-1-(3,5-dibromophenyl)-5-pyrazolecarboxamide.
1-(3,5-dimethylphenyl)-4-(2-methylallyl)oxycarbonyl-5-pyrazolecarboxamide.
4-(2-butenyl)oxycarbonyl-1-(3,5-dibromophenyl)-5-pyrazolecarboxamide.
4,5-dicarboxy-1-(3-chloro-5-methylphenyl)pyrazole, bis(triethylamine) salt.
4-(3-butenyl)oxycarbonyl-1-(3,5-dichlorophenyl)-5-pyrazolecarboxamide.
1-(3-bromo-5-chlorophenyl)-4-propargyloxycarbonyl-5-pyrazolecarboxamide.
1-(3-bromo-5-methylphenyl)-4-propargyloxycarbonyl-5-pyrazolecarboxamide.
1-(3-bromo-5-chlorophenyl)-4-(2-butynyl)oxycarbonyl-5-pyrazolecarboxamide.
1-(3-bromo-5-methylphenyl)-4-(1-methylpropargyl)oxycarbonyl-5-pyrazolecarboxamide.
4,5-dicarboxy-1-(3-chloro-5-methylphenyl)pyrazole.
1-(3-chloro-5-methylphenyl)-4,5-pyrazoledicarboximide.
1-(3,5-dimethylphenyl)-4,5-pyrazoledicarboximide.
1-(3,5-dibromophenyl)-4,5-pyrazoledicarboximide.
1-(3,5-dichlorophenyl)-4,5-pyrazoledicarboximide.
4,5-dicarboxy-1-(3,5-dichlorophenyl)pyrazole, bis(tetrabutylammonium) salt.
4,5-dicarboxy-1-(3-chloro-5-bromophenyl)pyrazole, bis(hexadecyl-trimethylammonium) salt.
4,5-dicarboxy-1-(3,5-dimethylphenyl)pyrazole, bis-(undecyl-triethylammonium) salt.
1-(3-chloro-5-methylphenyl)-4,5-pyrazoledicarboximide.
1-(3-bromo-5-methylphenyl)-4,5-pyrazoledicarboximide.
1-(3-bromo-5-chlorophenyl)-4,5-pyrazoledicarboximide.
4-carboxy-1-(3,5-dichlorophenyl)-5-pyrazolecarboxamide, sodium salt.
1-(3,5-dibromophenyl)-4-carboxy-5-pyrazolecarboxamide, potassium salt.
4-carboxy-1-(3,5-dichlorophenyl)-5-pyrazolecarboxamide, lithium salt.
4-carboxy-1-(3-chloro-5-methylphenyl)-5-pyrazolecarboxamide, triethylamine salt.
4-carboxy-1-(3-chloro-5-methylphenyl)-5-pyrazolecarboxamide, methylamine salt.
4-carboxy-1-(3,5-dichlorophenyl)-5-pyrazolecarboxamide, butylamine salt.
4-carboxy-1-(3,5-dibromophenyl)-5-pyrazolecarboxamide, triethylamine salt.
4-carboxy-1-(3,5-dimethylphenyl)-5-pyrazolecarboxamide, triethanolamine salt.
4-carboxy-1-(3,5-dichlorophenyl)-5-pyrazolecarboxamide, tetrabutylammonium salt.
4-carboxy-1-(3-chloro-5-methylphenyl)-5-pyrazolecarboxamide, benzyl-triethylammonium salt.
1-(3-bromo-5-methylphenyl)-4-carboxy-5-pyrazolecarboxamide, dibutyl-diethylammonium salt.
4-carboxy-1-(3,5-dimethylphenyl)-5-pyrazolecarboxamide, tetramethylammonium salt.
4-carboxy-1-(3,5-dimethylphenyl)-5-pyrazolecarboxamide, dimethyl-bis(dodecyl)ammonium salt.
4-carboxy-1-(3,5-dichlorophenyl)-5-pyrazolecarboxamide, diethyl-methyl-octadecylammonium salt.
4-carboxy-1-(3,5-dibromophenyl)-5-pyrazolecarboxamide, heptadecyl-trimethylammonium salt.
4-carboxy-1-(3-bromo-5-methylphenyl)-5-pyrazolecarboxamide, dimethyl-propyl-tetradecylammonium salt.
1-(3,5-dibromophenyl)-4-carboxy-5-pyrazolecarboxamide, dimethyl-bis(pentadecyl)ammonium salt.

The compounds of the present invention are prepared by a basic process whose first step is the reaction of an aryl hydrazine with an alkyl (alkoxymethylene)cyanoacetate to prepare the corresponding 5-amino-1-phenyl-4-1H-pyrazolecarboxylate. Next, the aminopyrazole is converted to the corresponding 5-halopyrazolecarboxylate, which is then converted to the 5-cyanopyrazolecarboxylate. That compound is the key intermediate for the preparation of the present pollen formation inhibitors.

In the key step of the basic process, the 5-cyano-4-pyrazolecarboxylate is hydrolyzed with a strong base, preferably with potassium hydroxide, to prepare the desired 4-carboxy-5-pyrazolecarboxamide. The reaction scheme is illustrated below.

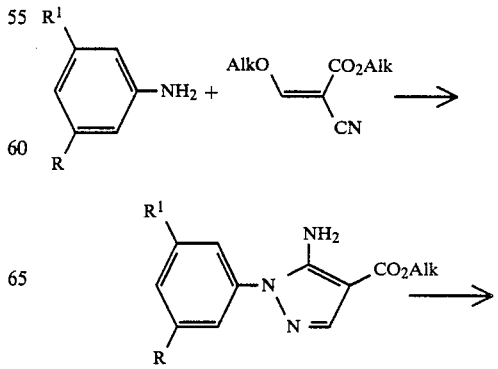

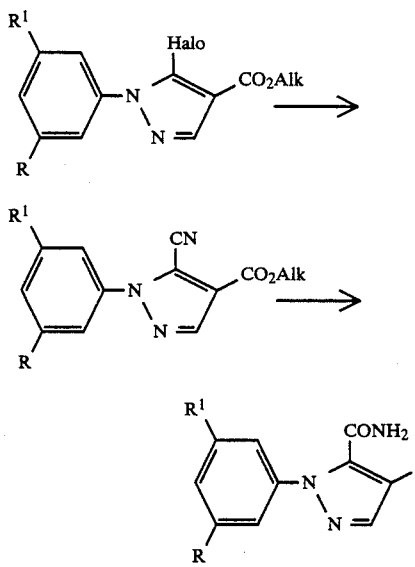

In the above scheme, the term Alk refers to $C_1$-$C_4$ alkyl groups, and the term Halo refers to chloro or bromo.

All of the steps of the processes described in this document proceed in acceptable yields without the use of unusual excess quantities of any reactant. In general, equimolar quantities can be used with satisfactory results. However, as is usual in organic reactions, it is preferable and advisable to use an excess amount of reactants which are inexpensive or easy to obtain, in order to assure full utilization of reactants which are expensive or difficult to obtain. Similarly, the steps of the process may be allowed to proceed for a long period of time, to maximize yield of the desired product, or may be halted before the reaction is complete, to maximize throughput of product from the system. Either manner of operating a process may be preferable, depending on the circumstances.

In the first step of the above scheme, it is most preferred to use a lower alkanol as the reaction solvent. The preferred reaction temperature is elevated, in the range of about 50°-150°. It will be understood that temperatures above the boiling point of the reaction mixture may be used at elevated pressures. However, the reactions will go at any reasonable temperature, such as about 0°-200°, if appropriate operating care is used.

The halogenation step of the above scheme is preferably carried out with nitrosyl chloride as both the diazotizing and halogenating agent, resulting in a 5-chloropyrazole. It is conventional to use nitrosyl chloride as a gas, by bubbling it through the vigorously mixed reaction mixture. The present chlorination is carried out in any non-reactive organic solvent, most preferably in a halogenated alkane such as chloroform, carbon tetrachloride and the like. Moderate temperatures in the range of 0°-50° are preferred, in order to maximize the solubility of nitrosyl chloride in the reaction mixture.

5-Bromopyrazole intermediates are prepared with an alkyl nitrite as the diazotizing agent, and an appropriate halogen source. Isoamyl nitrite, t-butyl nitrite and the like are appropriate diazotizing agents, and bromoform and elemental bromine are convenient sources of bromine. The reaction conditions are substantially the same as those for chlorinations.

Cyanation of the 5-halopyrazole is carried out in a conventional manner with an alkali metal cyanide, such as sodium cyanide, lithium cyanide or potassium cyanide. The cyanation can be done in inert organic solvents of which aprotic solvents are preferred. For example, dimethylformamide, dimethylsulfoxide and hexamethylphosphoramide are particularly preferred solvents in this step. It is preferred to cyanate at elevated temperatures in the range of about 50°-200°, most preferably about 80°-140°.

The hydrolysis step, which prepares the 4-carboxy-5-pyrazolecarboxamide, is most conveniently carried out with potassium hydroxide in aqueous ethanol. Conventionally, the base is dissolved in a minimum amount of water, and added to ethanol to prepare the reaction medium. Other alkali metal hydroxides, such as sodium hydroxide and lithium hydroxide, are also useful for the process. Similarly, other reaction solvents besides aqueous ethanol are useful, particularly other aqueous alkanols such as methanol, propanol and isopropanol. The hydrolysis is preferably carried out at a moderately elevated temperature in the range of about 50°-100°, most preferably at the reflux temperature of the reaction mixture.

Alternatively, the hydrolysis may be done with aqueous hydrobromic acid, at moderately elevated temperatures, such as 50°-100°. Continued hydrolysis with hydrobromic acid will hydrolyze the carboxamide group and prepare the dicarboxy compound. The dicarboxy compounds can thus be made in a single step from the 5-cyano-4-pyrazolecarboxylate, or can be made in a separate step from the 4-carboxy-5-pyrazolecarboxamide.

An improved method of preparing certain alkylaryl hydrazines, particularly phenylhydrazines having a 3-methyl substituent, is carried out by reacting the corresponding aniline with sodium nitrite to prepare the diazonium salt, and reacting the salt with potassium sulfite as described in Houben-Weyl, Methoden der Organische Chemie, Vol. 10/2, p. 180 (1967). The preparation below illustrates the preparation of an aryl hydrazine by the process just described.

An alternative process for the present compounds, which is preferable in some instances, begins with the 5-aminopyrazole-4-carboxylate. That intermediate is reacted with dimethyldisulfide in the presence of t-butyl nitrite in an inert organic solvent at a moderate temperature. Ambient temperature is quite satisfactory. The amino group of the intermediate is replaced by a methylthio group in that step. The sulfur atom of the methylthio group is then oxidized, to form a methylsulfonyl group, with an oxidizing reagent such as hydrogen peroxide. The oxidation is preferably carried out at a moderately elevated temperature in acetic acid.

The methylsulfonyl group of that intermediate is replaced with a nitrile group by reaction with an alkali metal cyanide at an elevated temperature, and the nitrile group is then hydrolyzed to form the amide as described in the outline of the basic process above.

The imides of the present invention are readily made by treating a 4-carboxy-5-pyrazolecarboxamide with a coupling agent at an elevated temperature. As shown in examples below, the preferred coupling agent is carbonyldiimidazole. Temperatures in the range of about 50°–150° are satisfactory, at normal or elevated pressure.

Salts of the 4-carboxy-5-pyrazolecarboxamides, or the 4,5-dicarboxypyrazoles, are readily prepared in the usual ways, as by contacting the compound with the appropriate base in an aqueous alkanol or aqueous ketone. When an alkali metal salt is desired, the base can be any appropriate alkali metal hydroxide, alkoxide, carbonate or bicarbonate. When a quaternary ammonium salt is to be made, the appropriate quaternary ammonium halide, sulfonate, hydroxide, methanesulfonate or the like is combined with the sodium salt of the carboxy compound in a suitable organic solvent. Salts are formed at moderate temperatures in the range of 0°–100°.

Compounds wherein the 4-carboxy group has been esterified are easily prepared in the usual manner, by reacting the 4-carboxy compound with the appropriate alcohol in an organic solvent, in the presence of a small amount of a mineral acid as esterification catalyst. Esters are also prepared by reacting an alkali metal salt of the acid with a halide of the ester group to be added. Moderate temperatures in the range of 50°–100° are quite satisfactory, and the reaction times are usually brief. Coupling agents may be used to assist esterifications but are not usually necessary.

The following preparation and examples are shown further to assist the reader in preparing the compounds of the present invention.

PREPARATION 1

3,5-dimethylphenylhydrazine, hydrochloride

To a 3-necked round-bottomed flask were added 250 ml of concentrated hydrochloric acid and 185 g of ice. To that mixture was added, over a period of 25 minutes, 100 g of 3,5-dimethylaniline. That mixture was held between 0°–5° and stirred for 15 minutes after the addition, and then a solution of 72 g of sodium nitrite in 230 ml of ice-water was added over 45 minutes while the mixture was held between −5° and 0°.

Meantime, a potassium sulfite solution was prepared by bubbling sulfur dioxide through a solution of 317 g of potassium hydroxide in 1,100 ml of water at 20°–30°. Sulfur dioxide was added to a final pH of 4. The solution was then cooled to 0°.

To the sulfite solution was added the diazonium salt mixture, and the mixture was heated to 85° and stirred for 1 hour at that temperature. It was then filtered while hot through a glass wool plug, and the filtrate was stirred while it cooled overnight to ambient temperature. It was then filtered, and the solids were dried in air overnight to obtain 185 g of crude product. It was dissolved in denatured ethanol and crystallized out by addition of water.

The product was then added to 875 ml of concentrated hydrochloric acid and 1,750 ml of ice-water. The mixture was heated to 75° and stirred for 30 minutes to form the hydrochloride salt. The reaction mixture was filtered hot, and stirred while cooling to ambient temperature overnight. The solids were collected by filtration and dried at 60° to obtain 39 g of the desired intermediate.

EXAMPLE 1

4-carboxy-1-(3,5-dimethylphenyl)-5-pyrazolecarboxamide

A 38.6 g portion of the intermediate prepared in Preparation 1 was combined with 37.9 g of ethyl (ethoxymethylene)cyanoacetate, 36.7 g of sodium acetate and 300 ml of ethanol, and the reaction mixture was heated under reflux for 20 hours. It was then poured into 1 liter of ice-water with stirring, and the mixture was filtered. The solids were dried, and were recrystallized from ethanol/water, with charcoal, to obtain 40.8 g of ethyl 5-amino-1-(3,5-dimethylphenyl)-4-pyrazolecarboxylate, m.p. 113°–114°.

A 30.6 g portion of that intermediate was added to 180 ml of chloroform, and 22.2 g of dimethyldisulfide was added. When the reactants had dissolved, 4.6 g of t-butyl nitrite was added at ambient temperature. The mixture warmed spontaneously to 35°, and another 4.6 g of the nitrite was added. That addition raised the temperature to 55°. The reaction temperature was maintained near 50° by addition of 1 ml portions of additional nitrite for one hour, until a total of 18.3 g of nitrite had been added. The mixture was then allowed to stir overnight while it cooled. The mixture was then washed twice with water and once with brine, and it was then dried using phase separation paper and sodium sulfate. The volatiles were then removed under vacuum to obtain 34.5 g of an oily residue. A 10.2 g portion of that residue was purified by high performance liquid chromatography, eluting with 3:1 hexane:ethyl acetate, to obtain 8.23 g of an oily product which was essentially pure ethyl 1-(3,5-dimethylphenyl)-5-methylthio-4-pyrazolecarboxylate.

A 7.3 g portion of the above intermediate was added to 30 ml of acetic acid and 15 ml of 30% hydrogen peroxide, and the mixture was heated on a steam bath for 105 minutes. It was then cooled overnight and filtered. The solids were washed with water and dried to obtain 5.6 g of ethyl 1-(3,5-dimethylphenyl)-5-methylsulfonyl-4-pyrazolecarboxylate, m.p. 120°–121.5°.

A 5.0 g portion of the above intermediate was combined with 35 ml of dimethylformamide and 1.9 g of sodium cyanide, and the mixture was heated to 80°–90° and held for 30 minutes. It was then stirred overnight while it cooled, and was poured into 100 ml of ice-water. The solids were separated by filtration and dried, and were recrystallized from ethanol/water to obtain 3.14 g of ethyl 5-cyano-1-(3,5-dimethylphenyl)-4-pyrazolecarboxylate, m.p. 83.5°–84.5°.

A 2.5 g portion of the above intermediate was added to 25 ml of ethanol, and 1.6 g of potassium hydroxide was added. The mixture was heated under reflux for 10 minutes, 7 ml of water was added, and the mixture was heated under reflux for 1.5 hours. It was then poured into 100 ml of water, and the mixture was made acid with hydrochloric acid. The mixture was chilled overnight, and was filtered. The solids were dried, dissolved in 2 N sodium hydroxide and made acidic with hydrochloric acid. The solids were collected, and were recrystallized from 400 ml of water to obtain 1.42 g of the desired product, m.p. 223°–225°.

Theory: C, 60.23; H, 5.05; N, 16.21;
Found: C, 60.39; H, 4.89; N, 15.92.

EXAMPLE 2

4-carboxy-1-(3,5-dichlorophenyl)-5-pyrazolecarboxamide

Twenty-five g of 3,5-dichlorophenylhydrazine, hydrochloride was added to 200 ml of ethanol, 18 g of sodium acetate and 18.6 g of ethyl (ethoxymethylene)cyanoacetate. The mixture was heated under reflux for 20 hours, and was poured into 700 ml of ice-water. The mixture was filtered, and the solids were dried and recrystallized from ethanol to obtain 28.5 g of ethyl 5-amino-1-(3,5-dichlorophenyl)-5-pyrazolecarboxylate, m.p. 157°–158°.

A 14.2 g portion of the above intermediate was added to 140 ml of chloroform, and to the mixture were added 8.9 g of dimethyldisulfide and 3.6 g of t-butyl nitrite at ambient temperature. A total of 3.6 g more of the nitrite was added in portions, and the mixture was then stirred overnight at ambient temperature. It was then washed twice with water and once with brine and was dried and evaporated under vacuum. The resulting oil was chromatographed with 7:2 hexane:ethyl acetate, and the product was recrystallized from hexane to obtain 10.0 g of ethyl 1-(3,5-dichlorophenyl)-5-methylthio-4-pyrazolecarboxylate, m.p. 70°–72°.

A 9.3 g portion of that intermediate was oxidized with 20 ml of 30% hydrogen peroxide in 40 ml of acetic acid, as shown in Example 1, to obtain 7.6 g of ethyl 1-(3,5-dichlorophenyl)-5-methylsulfonyl-4-pyrazolecarboxylate, m.p. 179°–181°.

A 7.0 g portion of the above intermediate was added to 60 ml of dimethylformamide and 2.4 g of sodium cyanide and reacted as shown in Example 1 to obtain 5.7 g of ethyl 1-(3,5-dichlorophenyl)-5-cyano-4-pyrazolecarboxylate, m.p. 101°–103°.

A 2.02 g portion of the above intermediate was dissolved in 40 ml of ethanol, and 1.1 g of potassium hydroxide was added. The mixture was stirred under reflux for 15 minutes, 20 ml of water was added, and the mixture was stirred under reflux for 80 minutes. It was then poured into 150 ml of water and filtered, and the filtrate was made acid with hydrochloric acid. The acidic solution was chilled overnight and filtered, and the solids were dried and recrystallized from aqueous acetic acid to obtain 1.4 g of the desired product, m.p. 258°–260° dec.

Theory: C, 44.03; H, 2.35; N, 14.00
Found: C, 44.27; H, 2.29; N, 13.93.

EXAMPLE 3

4-methoxycarbonyl-1-(3,5-dimethylphenyl)-5-pyrazolecarboxamide

A 1.1 g portion of the compound of Example 1 was suspended in 20 ml of methanol and hydrogen chloride gas was bubbled through the mixture for 1 minute. The mixture was then heated under reflux for 2 hours, and was poured into 50 ml of ice-water. The aqueous mixture was made basic with sodium hydroxide and was filtered, and the solids were dried under vacuum and recrystallized from toluene to obtain 0.14 g of the desired product, m.p. 179°–180°.

Theory: C, 61.53; H, 5.53; N, 15.38;
Found: C, 61.76; H, 5.40; N, 15.11.

EXAMPLE 4

4-carboxy-1-(3,5-dimethylphenyl)-5-pyrazolecarboxamide, sodium salt

Two g of the compound of Example 1 was suspended in 20 ml of methanol, and 0.4 g of sodium methoxide was added slowly with stirring. The solution was filtered and evaporated to dryness under vacuum, and the residue was recrystallized from methanol/diethyl ether and dried under vacuum to obtain 0.65 g of the desired salt, m.p. 266°–268°.

Theory: C, 55.52; H, 4.30; N, 14.94;
Found: C, 55.27; H, 4.49; N, 14.66.

EXAMPLE 5

4-carboxy-1-(3,5-dimethylphenyl)-5-pyrazolecarboxamide, dimethyl-bis($C_{10}$–$C_{14}$ alkyl)ammonium salt A 3.13 g portion of the compound of Example 1 was slurried in 60 ml of 50% aqueous acetone, and 0.48 g of sodium hydroxide was added. The mixture was warmed, and to it was added 7.48 g of Kemamine Q (Humko Chemical Division of Witco Chemical Company), a 75% solution of dimethyl-bis($C_{10}$–$C_{14}$ alkyl)ammonium chloride. The mixture was stirred overnight at ambient temperature, and the acetone was then removed under vacuum. The aqueous suspension was extracted with 100 ml of dichloromethane, and the organic layer was dried over sodium sulfate and evaporated under vacuum to obtain 7.28 g of the desired product in the form of an oil. It was identified by elemental and nuclear magnetic resonance analysis.

Found: C, 70.82; H, 11.14; N, 7.35.
NMR in $CDCl_3$: $\delta$ 7.95 (s,1H); 7.22 (s,2H); 6.92 (s,1H); 3.05–3.40 (m,4H); 3.19 (s,6H); 2.33 (s,6H); 0.7–1.7 (m,49H).

EXAMPLE 6

1-(3,5-dimethylphenyl)-4,5-pyrazoledicarboximide

Two g of the compound of Example 1 was dissolved in 15 ml of dimethylformamide, and 1.38 g of carbonyl diimidazole was added. The mixture was heated on the steam bath for 3 hours, and was then poured into 150 ml of ice-water. The mixture was filtered, and the solids were dried under vacuum and recrystallized from acetic acid to obtain 0.88 g of the desired product, m.p. 233°–235°.

Theory: C, 64.72; H, 4.60; N, 17.42;
Found: C, 64.34; H, 4.57; N, 17.12.

EXAMPLE 7

1-(3,5-dichlorophenyl)-4-methoxycarbonyl-5-pyrazolecarboxamide

A 1.5 g portion of the compound of Example 2 was suspended in 30 ml of methanol, and hydrogen chloride gas was bubbled through the suspension for 1 minute. Then 30 ml of methanol was added over a 5 minute period while the addition of gas was continued. Then the mixture was heated under reflux for 2 hours, and was cooled and filtered. The solids were collected and dried to obtain 1.15 g of the desired product, m.p. 220°–222°.

Theory: C, 45.88; H, 2.89; N, 13.38;
Found: C, 46.09; H, 3.06; N, 13.51.

EXAMPLE 8

1-(3,5-dichlorophenyl)-4-ethoxycarbonyl-5-pyrazolecarboxamide

Two g of the compound of Example 2 was suspended in 80 ml of absolute ethanol and hydrogen chloride 9as was bubbled through for 5 minutes. The mixture was then heated under reflux for 2 hours and cooled, and was then filtered. The solids were collected and dried to obtain 1.25 g of the desired product, m.p. 164°–166°.

Theory: C, 47.58; H, 3.38; N, 12.80;
Found: C, 47.49; H, 3.38; N, 12.69.

EXAMPLE 9

4-carboxy-1-(3,5-dichlorophenyl)-5-pyrazolecarboxamide, sodium salt

A 2.5 g portion of the compound of Example 2 was slurried in 25 ml of methanol, and 0.45 g of sodium methoxide was added with stirring. A little more methanol was added, and the mixture was heated on the steam bath for a few minutes. It was then cooled and filtered, and the filtrate was evaporated under vacuum to obtain the impure product, which was dissolved in hot methanol, treated with charcoal and precipitated with diethyl ether to obtain 1.26 g of the desired product, m.p. 278°–280°. The product was identified by nuclear magnetic resonance analysis.

NMR in DMSOd$_6$: δ 7.98 (s,1H); 7.72 (s,1H); 7.56 (s,2H).

EXAMPLE 10

4-carboxy-1-(3,5-dichlorophenyl)-5-pyrazolecarboxamide, dimethyl-bis($C_{10}$–$C_{14}$ alkyl)ammonium salt Five g of the compound of Example 2 was slurried in 100 ml of 50% aqueous acetone, and 0.67 g of sodium hydroxide was added. The mixture was warmed, and 10.35 g of Kemamine Q was added. The mixture was then stirred overnight at ambient temperature, and the acetone was removed under vacuum. The aqueous residue was extracted with dichloromethane, and the organic layer was evaporated under vacuum to obtain 11.3 g of an oil, which was identified as the desired product by elemental and nuclear magnetic resonance analysis.

Found: C, 63.98; H, 9.43; N, 7.13.

NMR in CDCl$_3$: δ8.00 (s,1H); 7.24 (s,3H); 3.05–3.55 (m,10H); 0.7–1.7 (m,54H).

EXAMPLE 11

4-carboxy-1-(3,5-dichlorophenyl)-5-pyrazolecarboxamide, octadecyl-trimethyl ammonium salt Five g of the compound of Example 2 was slurried in 100 ml of 50% aqueous acetone, 0.67 g of sodium hydroxide was added, and the mixture was warmed and stirred for 15 minutes. Then 10.6 g of octadecyl-trimethylammonium chloride, 50% solution, was added and the mixture was stirred overnight. It was then extracted with 100 ml of ethyl acetate, and the organic layer was washed with brine and dried with sodium sulfate and phase separation paper. The extract was then evaporated under vacuum to obtain 9.95 g of the desired product, m.p. 141°–144°. It was identified by elemental and nuclear magnetic resonance analysis.

Found: C, 60.55; H, 8.62; N, 8.44.

NMR in CDCl$_3$: δ 8.04 (s,1H); 7.32 (s,1H); 7.28 (s,2H); 3.08–3.44 (m,11H); 0.7–1.7 (m,38H).

EXAMPLE 12

1-(3,5-dichlorophenyl)-4,5-pyrazoledicarboximide

Four g of the compound of Example 2 was dissolved in 40 ml of dimethylformamide, and 2.38 g of carbonyldiimidazole was added. The mixture was stirred briefly, and was then heated on the steam bath for 3 hours. It was then poured into 200 ml of ice-water, and the mixture was filtered. The solids were dried and recrystallized from acetic acid-water to obtain 1.67 g of the desired product, m.p. 210°–212°.

Theory: C, 46.84; H, 1.79; N, 14.90;
Found: C, 47.07; H, 1.75; N, 14.85.

EXAMPLE 13

4,5-dicarboxy-1-(3,5-dichlorophenyl)pyrazole

A suspension of 6.25 g of ethyl 5-cyano-1-(3,5-dichlorophenyl)-4-pyrazolecarboxylate in 100 ml of 48% d was stirred at reflux for 4½ hours. The mixture was cooled and filtered, and the solids were dried and recrystallized from toluene to obtain 3.25 g of the desired product, m.p. 205° dec.

Theory: C, 43.88; H, 2.01; N, 9.30;
Found: C, 44.03; H, 2.28; N, 9.39.

The following reports of biological tests illustrate the efficacy of the present invention.

TEST I

The test was begun by planting Waldron wheat seeds in 4 inch pots, 4 seeds per pot, in a sterilized sandy-loam soil. The wheat was allowed to grow in a favorable greenhouse environment, and the plants were treated with a test compound about 24 days after the seed was planted. Each compound was formulated for testing by dissolving the proper amount, depending on the concentration to be tested, in 5 ml of 1:1 by volume acetone:denatured alcohol, containing 10% by volume of polysorbate 20. Compounds which did not dissolve were finely dispersed in the solvent. The organic mixture was then diluted to 30 ml with deionized water at about ambient temperature, and the aqueous dispersion was evenly sprayed over the foliage of two pots of wheat. Untreated control plants were provided in each experiment.

The results of the tests are reported below as the number of seed per spikelet. The number of seed per spikelet in a normal plant is about 1.5 to 2.5. In the tables below, the results of replicate experiments have been averaged. When the results of an experiment were not different from the results of the contemporaneous untreated controls, the inactivity is indicated merely by "N".

TABLE I

| Compound of Example No. | Concentration ppm | Result |
|---|---|---|
| 1 | 10 | N |
|  | 25 | 0.73 |
|  | 50 | 0.03 |
|  | 50 | 1.08 |
|  | 50 | N |
|  | 50 | 0.00 |
|  | 63 | 0.74 |
|  | 100 | 0.00 |
|  | 100 | N |
|  | 100 | 0.46 |
|  | 125 | 0.01 |
|  | 150 | 0.00 |
|  | 150 | 0.17 |
|  | 150 | 0.00 |
|  | 200 | 0.00 |
|  | 200 | N |
|  | 200 | N |
|  | 200 | N |
|  | 200 | N |
|  | 200 | 0.44 |
|  | 200 | 0.00 |
|  | 250 | 0.00 |
|  | 400 | 0.00 |
|  | 400 | 0.02 |
|  | 400 | 0.15 |
|  | 400 | 0.00 |
|  | 500 | 0.50 |
|  | 500 | 0.01 |
|  | 600 | 0.00 |
|  | 600 | 0.07 |
|  | 600 | 0.00 |
|  | 1000 | 0.00 |
|  | 1000 | 0.00 |
| 2 | 10 | 1.61 |
|  | 25 | 1.40 |
|  | 50 | 0.00 |
|  | 50 | 0.86 |

TABLE I-continued

| Compound of Example No. | Concentration ppm | Result |
| --- | --- | --- |
|  | 50 | 0.42 |
|  | 50 | N |
|  | 63 | 0.35 |
|  | 63 | 0.45 |
|  | 100 | 0.00 |
|  | 100 | 0.58 |
|  | 100 | 0.33 |
|  | 125 | 0.08 |
|  | 125 | 0.09 |
|  | 150 | 0.00 |
|  | 150 | 0.09 |
|  | 150 | 0.00 |
|  | 200 | 0.00 |
|  | 200 | 0.07 |
|  | 200 | N |
|  | 200 | N |
|  | 200 | N |
|  | 200 | 0.03 |
|  | 200 | 0.00 |
|  | 250 | 0.00 |
|  | 250 | 0.11 |
|  | 400 | 0.00 |
|  | 400 | 0.03 |
|  | 400 | 0.07 |
|  | 400 | 0.00 |
|  | 500 | 0.01 |
|  | 500 | 0.48 |
|  | 500 | 0.00 |
|  | 600 | 0.00 |
|  | 600 | 0.11 |
|  | 600 | 0.00 |
|  | 1000 | 0.00 |
|  | 1000 | 0.02 |
| 3 | 50 | 0.03 |
|  | 150 | N |
|  | 200 | N |
|  | 400 | 0.10 |
|  | 600 | 0.19 |
|  | 1000 | 0.00 |
| 4 | 50 | N |
|  | 50 | 0.00 |
|  | 150 | N |
|  | 150 | 0.00 |
|  | 200 | N |
|  | 200 | 0.00 |
|  | 400 | N |
|  | 400 | 0.00 |
|  | 600 | N |
|  | 600 | 0.00 |
|  | 1000 | N |
|  | 1000 | 0.00 |
| 5 | 25 | 0.39 |
|  | 50 | 0.28 |
|  | 100 | 0.16 |
|  | 200 | 0.00 |
|  | 400 | 0.00 |
|  | 600 | 0.00 |
|  | 800 | 0.00 |
| 6 | 50 | N |
|  | 50 | N |
|  | 150 | 0.83 |
|  | 150 | N |
|  | 200 | 0.49 |
|  | 200 | 0.00 |
|  | 400 | 0.12 |
|  | 400 | 0.00 |
|  | 600 | 0.00 |
|  | 600 | 0.00 |
|  | 1000 | 0.00 |
|  | 1000 | 0.00 |
| 7 | 50 | N |
|  | 100 | 0.74 |
|  | 150 | 0.00 |
|  | 200 | 0.38 |
|  | 400 | 0.00 |
|  | 500 | 0.31 |
|  | 600 | 0.27 |
|  | 1000 | N |
| 8 | 50 | 0.36 |
|  | 150 | 0.59 |
|  | 200 | 0.13 |
|  | 400 | 1.24 |
|  | 600 | 0.36 |
|  | 1000 | 0.29 |
| 9 | 50 | 0.20 |
|  | 50 | 0.00 |
|  | 150 | 0.14 |
|  | 150 | 0.00 |
|  | 200 | 0.10 |
|  | 200 | 0.00 |
|  | 400 | 0.04 |
|  | 400 | 0.00 |
|  | 600 | 0.06 |
|  | 600 | 0.00 |
|  | 1000 | 0.00 |
|  | 1000 | 0.00 |
| 10 | 25 | 0.83 |
|  | 50 | 0.19 |
|  | 100 | 0.71 |
|  | 200 | 0.00 |
|  | 400 | 0.00 |
|  | 600 | 0.00 |
|  | 1000 | 0.00 |
| 11 | 50 | N |
|  | 150 | 0.00 |
|  | 200 | 0.00 |
|  | 400 | 0.00 |
|  | 600 | 0.00 |
|  | 1000 | 0.00 |
| 12 | 50 | 1.83 |
|  | 150 | 1.53 |
|  | 200 | 1.35 |
|  | 400 | 0.82 |
|  | 600 | 0.77 |
|  | 1000 | 0.39 |

TEST II

The tests reported below were carried out in the same way as those reported in Test I, except that the formulated compounds were applied to the soil in which the wheat plants grew, rather than to the foliage. Applications were made about 21 days after the seed was planted.

TABLE II

| Compound of Example No. | Rate lb/A | Result |
| --- | --- | --- |
| 1 | 0.19 | 0.74 |
|  | 0.38 | 0.22 |
|  | 0.47 | 0.00 |
|  | 0.75 | 0.45 |
|  | 0.94 | 0.00 |
|  | 1.5 | 0.08 |
|  | 1.88 | 0.00 |
|  | 3 | 0.11 |
|  | 3.75 | 0.00 |
|  | 6 | 0.40 |
| 2 | 0.19 | 1.84 |
|  | 0.38 | 0.93 |
|  | 0.47 | 0.00 |
|  | 0.47 | 0.00 |
|  | 0.75 | 0.27 |
|  | 0.94 | 0.00 |
|  | 0.94 | 0.00 |
|  | 1.5 | 0.12 |
|  | 1.88 | 0.00 |
|  | 1.88 | 0.00 |
|  | 3 | 0.15 |
|  | 3.75 | 0.00 |
|  | 3.75 | 0.00 |
|  | 6 | 0.00 |

TEST III

The following tests were carried out in the same manner as those of Test I, except that the compounds were supplied in the form of formulations, the formulae of which are listed below in the Compositions section of this document.

TABLE III

| Compound of Example No. | Composition | Concentration ppm | Result |
|---|---|---|---|
| 1 | 1 | 63 | 0.88 |
|   |   | 125 | 0.00 |
|   |   | 250 | 0.03 |
|   |   | 500 | 0.00 |
| 2 | 2 | 63 | 0.49 |
|   |   | 125 | 0.06 |
|   |   | 250 | 0.00 |
|   |   | 500 | 0.00 |

TEST IV

The tests reported below were carried out in the same manner as those of Test II, except that the compounds were supplied as formulated compositions, and two varieties of wheat were used. The data are reported in the table below in the same manner described in Test I.

TABLE IV

| Cmpd. of Ex. No. | Composition | Variety | Rate lb/A | Result |
|---|---|---|---|---|
| 1 | 1 | Waldron | 0.47 | 0.00 |
|   |   |   | 0.94 | 0.00 |
|   |   |   | 1.88 | 0.00 |
|   |   |   | 3.75 | 0.00 |
|   | 3 | Yolo | 0.5 | 1.00 |
|   |   |   | 1.0 | 0.94 |
|   |   |   | 2.0 | 0.08 |
|   |   | Waldron | 0.5 | 1.70 |
|   |   |   | 1.0 | 0.91 |
|   |   |   | 2.0 | 1.02 |
| 2 | 2 | Waldron | 0.47 | 0.00 |
|   |   |   | 0.94 | 0.00 |
|   |   |   | 1.88 | 0.00 |
|   |   |   | 3.75 | 0.00 |
|   | 4 | Yolo | 0.5 | 1.41 |
|   |   |   | 1.0 | 0.37 |
|   |   |   | 2.0 | 0.19 |
|   |   | Waldron | 0.5 | 1.06 |
|   |   |   | 1.0 | 0.59 |
|   |   |   | 2.0 | 0.20 |

TEST V

Tests which were substantially similar to those of Test I were carried out on barley. The applications of compounds were made about 21 days after the barley seeds were planted. The results were as followed.

TABLE V

| Cmpd. of Ex. No. | Variety | Concentration ppm | Result |
|---|---|---|---|
| 1 | Poco | 12.5 | N |
|   |   | 25 | N |
|   |   | 50 | N |
|   |   | 100 | N |
|   |   | 200 | N |
|   |   | 400 | N |
|   |   | 1000 | 0.43 |
|   | Barcott | 12 | N |
|   |   | 25 | N |
|   |   | 50 | N |
|   |   | 100 | N |
|   |   | 200 | N |
|   |   | 400 | N |
|   |   | 1000 | 0.00 |
| 2 | Poco | 12.5 | N |
|   |   | 25 | N |
|   |   | 50 | N |
|   |   | 100 | 0.16 |
|   |   | 200 | 0.31 |
|   |   | 400 | 0.10 |
|   |   | 1000 | 0.12 |
|   | Barcott | 12 | N |
|   |   | 25 | N |
|   |   | 50 | N |
|   |   | 100 | N |
|   |   | 200 | N |
|   |   | 400 | 0.00 |
|   |   | 1000 | 0.00 |

TEST VI

Tests with barley were carried out according to the method of Test II above; the compounds were applied to the soil about 21 days after the barley seeds were planted.

TABLE VI

| Cmpd. of Ex. No. | Variety | Rate lb/A | Result |
|---|---|---|---|
| 1 | Poco | 0.19 | N |
|   |   | 0.38 | N |
|   |   | 0.75 | N |
|   |   | 1.5 | N |
|   |   | 3 | 0.00 |
|   |   | 6 | 0.10 |
|   |   | 15 | 0.00 |
|   | Barcott | 0.19 | N |
|   |   | 0.38 | N |
|   |   | 0.75 | N |
|   |   | 1.5 | 0.04 |
|   |   | 3 | 0.18 |
|   |   | 6 | 0.02 |
|   |   | 15 | 0.00 |
| 2 | Poco | 0.19 | N |
|   |   | 0.38 | N |
|   |   | 0.75 | N |
|   |   | 1.5 | 0.39 |
|   |   | 3 | N |
|   |   | 6 | 0.49 |
|   |   | 15 | 0.10 |
| 2 | Barcott | 0.19 | N |
|   |   | 0.38 | N |
|   |   | 0.75 | N |
|   |   | 1.5 | 0.15 |
|   |   | 3 | 0.08 |
|   |   | 6 | 0.02 |
|   |   | 15 | 0.01 |

TESTS VII

The tests reported below were carried out on barley. The compounds were provided in the form of formulated granular compositions, which were applied at the time the seeds were planted, by mixing the granules into the top few millimeters of soil in each pot.

TABLE VII

| Cmpd. of Ex. No. | Composition | Variety | Rate lb/A | Result |
|---|---|---|---|---|
| 1 | 3 | Bonanza | 0.5 | 0.33 |
|   |   |   | 1.0 | 0.41 |
|   |   |   | 2.0 | 0.32 |
|   |   | Gateway | 0.5 | 0.01 |
|   |   |   | 1.0 | 0.26 |
|   |   |   | 2.0 | 0.50 |

TABLE VII-continued

| Cmpd. of Ex. No. | Composition | Variety | Rate lb/A | Result |
|---|---|---|---|---|
| | | Poco | 0.5 | 0.18 |
| | | | 1.0 | 0.10 |
| | | | 2.0 | 0.42 |
| 2 | 4 | Bonanza | 0.5 | 0.09 |
| | | | 1.0 | 0.49 |
| | | | 2.0 | 0.00 |
| | | Gateway | 0.5 | 0.15 |
| | | | 1.0 | 0.02 |
| | | | 2.0 | 0.01 |
| | | Poco | 0.5 | 0.17 |
| | | | 1.0 | 0.25 |
| | | | 2.0 | 0.14 |

TEST VIII

Golden Midget corn seeds were planted in pots, and the plants were grown in the greenhouse. Applications of compounds of the invention were made in the form of foliar sprays, about 15 days after the seeds were planted. In some tests, the compounds were applied in the form of dispersions such as were described in Test I above; in other tests, the compounds were in the form of formulated compositions. Concentrations as high as 10,300 ppm were tested. In all cases, foliar spray applications failed to produce sterile pollen from the treated plants.

TEST IX

Further tests on corn were carried out in the greenhouse, by applying the compounds to the soil in the 8-inch pots in which the plants grew, 2-3 days after the seeds were planted. In some cases, the compounds were formulated as described in Test I, and in others, they were in the form of compositions described in the Compositions section below. When the compounds were inactive, and the treated plants produced viable pollen, the fact is indicated in the table below by "N". Activity, observed as sterile pollen, is indicated by a "A", and, in some instances, further observations about the condition of the treated plants. In all tests, the corn was of the Golden Midget variety.

TABLE IX

| Cmpd. of Ex. No. | Composition | Rate mg/pot | Result |
|---|---|---|---|
| 1 | 1 | 7.5 | N |
| | | 15 | A Sterile tassel |
| | | 20 | A Sterile tassel |
| | | 25 | A Sterile tassel |
| | | 30 | A Sterile tassel |
| | | 10 | A Good ear |
| | | 20 | A Reduced seed |
| | | 40 | A Reduced seed |
| | | 10 | A Stunted ears |
| | | 20 | A Good ear |
| | | 40 | A Slt. ear injury |
| | 3 | 4.5 | N |
| | | 9.1 | A Pollen not viable |
| | | 18.1 | A Sterile tassel |
| | | 36.3 | A No anthers |
| | | 72.6 | A No tassel |
| | | 4.5 | N |
| | | 9.1 | N |
| | | 18.1 | A Sterile tassel |
| | | 36.3 | A Sterile tassel |
| | | 72.6 | A Sterile tassel |
| | | 4.5 | N |
| | | 9.1 | A No anthers |
| | | 18.1 | A Sterile tassel |
| | | 36.3 | A Sterile tassel |

TABLE IX-continued

| Ex. No. | Composition | lb/A | Result |
|---|---|---|---|
| 1 | 3 | 72.6 | A Sterile tassel |
| | Test 1 | 10 | N |
| | | 20 | A Few anthers |
| | | 40 | A No tassel |
| | | 10 | N |
| | | 20 | A Sterile tassel |
| | | 40 | A No tassel |
| | | 10 | A Damaged tassel |
| | | 20 | A Sterile tassel |
| | | 40 | A No tassel |
| | | 10 | N |
| | | 20 | A Sterile tassel |
| | | 40 | A Sterile tassel |
| | | 4.2 | N |
| | | 8.5 | N |
| | | 17 | A No tassel or injured tassel |
| 2 | Test 1 | 9.1 | N |
| | | 18.1 | N |
| | | 36.3 | N |
| | | 72.6 | N |
| | | 10 | N |
| | | 20 | N |
| | | 40 | N |
| 2 | 4 | 20 | N |
| | | 40 | N |
| | | 60 | N |
| | | 20 | N |
| | | 40 | N |
| | | 60 | A Sterile tassel |
| | 2 | 20 | N |
| | | 40 | N |
| | | 60 | N |
| | | 20 | N |
| | | 40 | N |
| | | 60 | N |
| | Test 1 | 4.5 | N |
| | | 9.1 | N |
| | | 18.1 | A Damaged tassel |
| | | 36.3 | N |
| | | 72.6 | N |
| | | 4.5 | N |
| | | 9.1 | N |
| | | 18.1 | N |
| | | 36.3 | N |
| | | 72.6 | N |
| 3 | Test 1 | 10 | A No tassel |
| | | 40 | A No tassel |
| 4 | Test 1 | 10 | N |
| | | 20 | N |
| | | 40 | A Damaged tassel |
| | | 10 | N |
| | | 20 | A No tassel |
| | | 40 | A Damaged tassel |
| 5 | Test 1 | 10 | N |
| | | 20 | N |
| | | 40 | N |
| | | 10 | N |
| | | 20 | N |
| | | 40 | A No tassel |
| | | 10 | N |
| | | 20 | N |
| | | 40 | A Slow tassel |
| | | 10 | N |
| | | 20 | N |
| | | 40 | A Slow tassel |

Tests of compounds 5–12, substantially like those applied to the compound of Example 5, showed no activity.

TEST X

The experiment described here was a field experiment carried out in central Indiana, U.S.A. The experiment was started by planting strips of Pioneer and Caldwell wheat in the autumn. The field was fertilized at the time of planting, and the wheat was planted in long strips of a few rows each, adjacent to one another, so that pollen could readily be transferred from one group of plants to another.

The test compounds were those of Examples 1 and 2, formulated as Compositions 1 and 2, respectively. The compounds were applied diluted in water, as foliar sprays. Volume rates of 50 and 100 gallons per acre were used, as shown in the table below.

One application of compound was made to each test plot. Applications were made on 9 different dates, all in the month of April, following the planting of the wheat.

The test plots were laid out in the bands of wheat, and they became the female plots for the production of hybrid wheat. Each test plot was 6 rows X 13 feet in size.

At the time of wheat head emergence, some heads in each treated plot were bagged with small glassine bags. Five heads in each row of each test plot were bagged.

When the seed was formed, the number of seeds per spikelet in the bagged plants gave a measure of the extent to which pollen formation was inhibited, because those seed could have been formed only by self-pollination. Thus, the number of seeds per spikelet is a measure of the degree of hybridization which could occur If the number is zero, then complete hybridization will occur. If the number is larger, between zero and the number of seeds per spikelet in the control plants, the degree of hybridization is correspondingly reduced.

In the table below, the results are reported as the number of seeds per spikelet in the bagged heads. Only the results from the main shoots of each plant are considered; tiller results are not reported. The average results for a large number of untreated control plots are also given for each variety of wheat.

TABLE X

| Cmpd. of Ex. No. | Rate lb/A | Volume gal/A | Date | Result |
|---|---|---|---|---|
| Caldwell Wheat | | | | |
| Control | (mean of 13 plots) | | | 1.74 |
| 1 | 0.25 | 50 | 1 | 0.22 |
| | | | 2 | 0.36 |
| | | | 3 | 0.82 |
| | | | 4 | 0.73 |
| | | | 5 | 1.45 |
| | | | 6 | 0.07 |
| | | | 7 | 0.16 |
| | | | 8 | 0.00 |
| | | | 9 | 0.05 |
| | | 100 | 1 | 1.45 |
| | | | 2 | 0.82 |
| | | | 3 | 0.61 |
| | | | 4 | 1.35 |
| | | | 5 | 1.31 |
| | | | 6 | 0.61 |
| | | | 7 | 0.09 |
| | | | 8 | 0.12 |
| | | | 9 | 0.00 |
| | 0.5 | 50 | 1 | 0.05 |
| | | | 2 | 0.52 |
| | | | 3 | 0.57 |
| | | | 4 | 0.10 |
| | | | 5 | 0.59 |
| | | | 6 | 0.00 |
| | | | 7 | 0.35 |
| | | | 8 | 0.00 |
| | | | 9 | 0.00 |
| 1 | 0.5 | 100 | 1 | 0.36 |
| | | | 2 | 0.02 |
| | | | 3 | 0.27 |
| | | | 4 | 0.23 |
| | | | 5 | 0.24 |
| | | | 6 | 0.00 |
| | | | 7 | 0.00 |
| | | | 8 | 0.00 |

TABLE X-continued

| Cmpd. of Ex. No. | Rate lb/A | Volume gal/A | Date | Result |
|---|---|---|---|---|
| | | | 9 | 0.00 |
| | 1 | 50 | 1 | 0.00 |
| | | | 2 | 0.00 |
| | | | 3 | 0.01 |
| | | | 4 | 0.00 |
| | | | 5 | 0.00 |
| | | | 6 | 0.00 |
| | | | 7 | 0.01 |
| | | | 8 | 0.21 |
| | | | 9 | 0.00 |
| | | 100 | 1 | 0.00 |
| | | | 2 | 0.12 |
| | | | 3 | 0.00 |
| | | | 4 | 0.05 |
| | | | 5 | 0.00 |
| | | | 6 | 0.01 |
| | | | 7 | 0.00 |
| | | | 8 | 0.00 |
| | | | 9 | 0.00 |
| 1 | 2 | 50 | 1 | 0.00 |
| | | | 2 | 0.00 |
| | | | 3 | 0.00 |
| | | | 4 | 0.01 |
| | | | 5 | 0.01 |
| | | | 6 | 0.01 |
| | | | 7 | 0.01 |
| | | | 8 | 0.01 |
| | | | 9 | 0.09 |
| | | 100 | 1 | 0.00 |
| | | | 2 | 0.00 |
| | | | 3 | 0.00 |
| | | | 4 | 0.00 |
| | | | 5 | 0.00 |
| | | | 6 | 0.00 |
| | | | 7 | 0.01 |
| | | | 8 | 0.00 |
| | | | 9 | 0.00 |
| 2 | 0.25 | 50 | 1 | 0.73 |
| | | | 2 | 1.13 |
| | | | 3 | 1.06 |
| | | | 4 | 1.59 |
| | | | 5 | 1.41 |
| | | | 6 | 1.43 |
| | | | 7 | 1.03 |
| 2 | 0.25 | 50 | 8 | 0.40 |
| | | | 9 | 0.55 |
| | | 100 | 1 | 1.02 |
| | | | 2 | 1.52 |
| | | | 3 | 1.92 |
| | | | 4 | 1.62 |
| | | | 5 | 1.86 |
| | | | 6 | 1.09 |
| | | | 7 | 0.89 |
| | | | 8 | 0.11 |
| | | | 9 | 0.64 |
| | 0.5 | 50 | 1 | 0.97 |
| | | | 2 | 0.60 |
| | | | 3 | 0.89 |
| | | | 4 | 1.61 |
| | | | 5 | 1.60 |
| | | | 6 | 1.07 |
| | | | 7 | 0.94 |
| | | | 8 | 0.55 |
| | | | 9 | 0.40 |
| | | 100 | 1 | 1.05 |
| | | | 2 | 1.05 |
| | | | 3 | 1.37 |
| | | | 4 | 2.10 |
| | | | 5 | 1.89 |
| | | | 6 | 0.49 |
| 2 | 0.5 | 100 | 7 | 0.37 |
| | | | 8 | 0.62 |
| | | | 9 | 0.84 |
| | 1 | 50 | 1 | 0.44 |
| | | | 2 | 0.69 |
| | | | 3 | 0.23 |
| | | | 4 | 0.71 |
| | | | 5 | 1.65 |
| | | | 6 | 1.10 |
| | | | 7 | 0.45 |

TABLE X-continued

| Cmpd. of Ex. No. | Rate lb/A | Volume gal/A | Date | Result |
|---|---|---|---|---|
| | | | 8 | 0.39 |
| | | | 9 | 0.34 |
| | | 100 | 1 | 0.68 |
| | | | 2 | 1.30 |
| | | | 3 | 0.86 |
| | | | 4 | 1.08 |
| | | | 5 | 2.16 |
| | | | 6 | — |
| | | | 7 | 0.47 |
| | | | 8 | 0.01 |
| | | | 9 | 0.04 |
| | 2 | 50 | 1 | 0.12 |
| | | | 2 | 0.50 |
| | | | 3 | 0.28 |
| | | | 4 | 0.05 |
| | | | 5 | 0.13 |
| | 2 | 50 | 6 | 0.40 |
| | | | 7 | 0.60 |
| | | | 8 | 0.15 |
| | | | 9 | 0.42 |
| | | 100 | 1 | 0.63 |
| | | | 2 | 0.26 |
| | | | 3 | 0.54 |
| | | | 4 | 0.22 |
| | | | 5 | 0.66 |
| | | | 6 | 0.20 |
| | | | 7 | 0.25 |
| | | | 8 | 0.10 |
| | | | 9 | 0.03 |
| | Pioneer Wheat | | | |
| Control | (mean of 14 plots) | | | 1.56 |
| 1 | 0.25 | 50 | 1 | 1.31 |
| | | | 2 | 1.12 |
| | | | 3 | 1.07 |
| | | | 4 | 1.61 |
| | | | 5 | 1.76 |
| | | | 6 | 0.80 |
| | | | 7 | 0.57 |
| | | | 8 | 0.71 |
| | | | 9 | 0.59 |
| | | 100 | 1 | 1.46 |
| | | | 2 | 1.64 |
| | | | 3 | 1.13 |
| | | | 4 | 1.28 |
| | | | 5 | 1.91 |
| | | | 6 | 1.48 |
| | | | 7 | 0.85 |
| | | | 8 | 0.32 |
| | | | 9 | 0.32 |
| | 0.5 | 50 | 1 | 0.32 |
| | | | 2 | 1.30 |
| | | | 3 | 1.01 |
| | | | 4 | 0.69 |
| | | | 5 | 1.08 |
| | | | 6 | 0.21 |
| | | | 7 | 0.76 |
| 1 | 0.5 | 50 | 8 | 0.12 |
| | | | 9 | 0.04 |
| | | 100 | 1 | 1.33 |
| | | | 2 | 0.42 |
| | | | 3 | 0.97 |
| | | | 4 | 1.07 |
| | | | 5 | 1.14 |
| | | | 6 | 0.33 |
| | | | 7 | 0.05 |
| | | | 8 | 0.01 |
| | | | 9 | 0.00 |
| | 1 | 50 | 1 | 0.02 |
| | | | 2 | 0.05 |
| | | | 3 | 0.17 |
| | | | 4 | 0.01 |
| | | | 5 | 0.05 |
| | | | 6 | 0.00 |
| | | | 7 | 0.05 |
| | | | 8 | 0.00 |
| | | | 9 | 0.00 |
| | | 100 | 1 | 0.41 |
| | | | 2 | 0.25 |
| | | | 3 | 0.61 |
| | | | 4 | 0.45 |
| | | | 5 | 0.02 |
| 1 | 1 | 100 | 6 | 0.22 |
| | | | 7 | 0.03 |
| | | | 8 | 0.02 |
| | | | 9 | 0.00 |
| | 2 | 50 | 1 | 0.00 |
| | | | 2 | 0.00 |
| | | | 3 | 0.03 |
| | | | 4 | 0.01 |
| | | | 5 | 0.00 |
| | | | 6 | 0.00 |
| | | | 7 | 0.01 |
| | | | 8 | 0.00 |
| | | | 9 | 0.01 |
| | | 100 | 1 | 0.00 |
| | | | 2 | 0.00 |
| | | | 3 | 0.08 |
| | | | 4 | 0.01 |
| | | | 5 | 0.02 |
| | | | 6 | 0.00 |
| | | | 7 | 0.00 |
| | | | 8 | 0.00 |
| | | | 9 | 0.00 |
| 2 | 0.25 | 50 | 1 | 0.73 |
| | | | 2 | 1.38 |
| | | | 3 | 1.05 |
| | | | 4 | 1.78 |
| | | | 5 | 1.83 |
| | | | 6 | 1.43 |
| | | | 7 | 0.75 |
| | | | 8 | 0.55 |
| | | | 9 | 0.70 |
| | | 100 | 1 | 1.45 |
| | | | 2 | 1.05 |
| | | | 3 | 0.67 |
| | | | 4 | 1.50 |
| | | | 5 | 1.61 |
| | | | 6 | 1.42 |
| | | | 7 | 0.71 |
| | | | 8 | 0.27 |
| | | | 9 | 0.60 |
| | 0.5 | 50 | 1 | 1.15 |
| | | | 2 | 0.73 |
| | | | 3 | 0.95 |
| | | | 4 | 1.51 |
| | | | 5 | 1.23 |
| | | | 6 | 0.73 |
| | | | 7 | 0.78 |
| | | | 8 | 0.29 |
| | | | 9 | 0.41 |
| 1 | 0.5 | 100 | 1 | 1.18 |
| | | | 2 | 1.36 |
| | | | 3 | 0.84 |
| | | | 4 | 1.56 |
| | | | 5 | 1.63 |
| | | | 6 | 0.55 |
| | | | 7 | 0.33 |
| | | | 8 | 0.51 |
| | | | 9 | 0.43 |
| 2 | 1 | 50 | 1 | 0.55 |
| | | | 2 | 0.57 |
| | | | 3 | 0.45 |
| | | | 4 | 0.96 |
| | | | 5 | 1.28 |
| | | | 6 | 0.64 |
| | | | 7 | 0.87 |
| | | | 8 | 0.10 |
| | | | 9 | 0.15 |
| | | 100 | 1 | 1.11 |
| | | | 2 | 1.01 |
| | | | 3 | 0.46 |
| | | | 4 | 1.08 |
| | | | 5 | 1.61 |
| | | | 6 | 0.25 |
| | | | 7 | 0.33 |
| | | | 8 | 0.23 |
| | | | 9 | 0.10 |
| 2 | 2 | 50 | 1 | 0.52 |
| | | | 2 | 0.59 |

TABLE X-continued

| Cmpd. of Ex. No. | Rate lb/A | Volume gal/A | Date | Result |
| --- | --- | --- | --- | --- |
|  |  |  | 3 | 0.38 |
|  |  |  | 4 | 0.69 |
|  |  |  | 5 | 0.36 |
|  |  |  | 6 | 0.61 |
|  |  |  | 7 | 0.51 |
|  |  |  | 8 | 0.00 |
|  |  |  | 9 | 0.40 |
| 2 | 2 | 100 | 1 | 0.92 |
|  |  |  | 2 | 0.40 |
|  |  |  | 3 | 0.92 |
|  |  |  | 4 | 0.27 |
|  |  |  | 5 | 0.64 |
|  |  |  | 6 | 0.32 |
|  |  |  | 7 | 0.21 |
|  |  |  | 8 | 0.07 |
|  |  |  | 9 | 0.00 |

TEST XI

This test was carried out by formulating compounds as shown in Test I, and applying the formulations to 4-inch pots of Waldron wheat. Applications were directly to the soil, about 16 days after the seeds were planted. The results are reported below in the manner of Table I above.

TABLE XI

| Compound of Example Number | Rate mg/pot | Result |
| --- | --- | --- |
| 8 | 1 | 0.00 |
|  | 0.5 | 0.00 |
|  | 0.25 | 0.42 |
|  | 0.12 | 0.23 |
| 13 | 1 | 0.00 |
|  | 0.5 | 0.30 |
|  | 0.25 | N |
|  | 0.12 | N |

TEST XII

Several compounds were tested on Golden Midget corn in the greenhouse. Plants were grown in 8" pots. The compounds were formulated substantially as shown in Test I, and the formulations were diluted so that the amounts shown in the table below were each applied in ml total volume. Applications were made to the soil, two days after planting.

As the plants matured, the development of the tassel and silk were rated on a scale where 0 indicated no development, and 100 indicated normal development. Even the controls did not develop normally, it will be noted, because of the greenhouse conditions. The time, in days after planting, when the anthers extruded was also noted. The following results were observed; all are means of three replicates.

TABLE XII

| Cpd. of Ex. No. | Rate mg/pot | Tassel Devel. | Silk Devel. | Anther Extrusion |
| --- | --- | --- | --- | --- |
| 1 | 1.88 | 86.7 | 35.0 | 47.3 |
|  | 3.75 | 46.7 | 90.0 | 30.3 |
|  | 7.5 | 43.3 | 80.0 | 18.0 |
|  | 15.0 | 5.7 | 41.7 | none |
|  | 30.0 | 7.3 | 51.7 | none |
| 2 | 15.0 | 93.3 | 53.3 | 49.7 |
|  | 30.0 | 80.0 | 63.3 | 47.7 |
|  | 60.0 | 49.0 | 93.3 | 32.3 |
| 3 | 0.25 | 100.0 | 20.0 | 47.7 |
|  | 0.50 | 93.3 | 80.0 | 48.0 |
|  | 1.0 | 76.7 | 93.3 | 47.0 |
|  | 2.0 | 61.7 | 56.7 | 33.0 |
|  | 4.0 | 23.3 | 20.0 | none |
| 4 | 1.88 | 60.0 | 90.0 | 48.3 |
|  | 3.75 | 63.3 | 93.3 | 46.0 |
|  | 7.5 | 38.3 | 58.3 | 47.7 |
|  | 15.0 | 21.7 | 71.7 | 34.3 |
|  | 30.0 | 15.7 | 31.7 | none |
| 5 | 5.0 | 91.7 | 66.7 | 47.3 |
|  | 10.0 | 51.7 | 66.7 | 32.3 |
|  | 20.0 | 31.7 | 35.0 | 32.0 |
|  | 40.0 | 17.7 | 58.3 | 36.3 |
|  | 80.0 | 7.3 | 15.0 | none |
| 7 | 15.0 | 35.0 | 75.0 | 30.3 |
|  | 30.0 | 66.7 | 40.0 | 47.7 |
|  | 60.0 | 55.0 | 58.3 | 34.3 |
| 9 | 15.0 | 95.0 | 38.3 | 47.0 |
|  | 30.0 | 68.3 | 38.3 | 46.3 |
|  | 60.0 | 61.7 | 61.7 | 51.0 |
| 10 | 36.5 | 86.7 | 60.0 | 45.3 |
|  | 73.0 | 80.0 | 41.7 | 49.0 |
|  | 146.0 | 73.0 | 3.3 | 33.7 |
| Control | 0 | 82.0 | 58.2 | 44.1 |

The compounds of this invention are useful for inhibiting pollen formation in cereal grain plants which are sensitive to such treatment, and the compositions in which the compounds are formulated for application, and the methods by which the compounds are applied to obtain the inhibition of pollen formation, constitute embodiments of the invention.

A compound must be supplied to the plant before the maturation of anthers. It must be noted that the head of a plant matures over a period of time, and different plants in a field mature at different times. Accordingly, a compound must be supplied before anther maturation in the most mature plants in the field to be treated, if best results are to be obtained.

In wheat anther maturation occurs while the plant's head is about 5-10 mm long. Thus, it is advisable to dissect representative plants from time to time to determine when development of the head, and therefore of the anthers, is approaching. Best results are obtained by supplying the compound when the head is less than 5-10 mm long. Comparable indications of development in other species are used to determine the proper time for treatment.

The compound must be supplied, not merely applied, to the plant before anther maturation. In this document, the term "supplying" is used to mean administering the compound in such a manner that it is absorbed by the plant and is available to the target organs. In all cases, the compound must be applied sufficiently early that it is absorbed and supplied to the plant before anther maturation.

In the practice of the present invention, it is necessary to apply an effective amount of a compound of the invention to the plant or the soil in which it grows. Effective amounts can be measured in terms of the concentration of the compound in a dispersion, when the compound is applied to the foliage, or, preferably, can be measured in terms of the amount of compound applied per unit area of land. The concentration of the compound is a useful measurement, because the amount of compound applied to foliage is limited by the amount of the dispersion which is retained by the foliage. That amount is substantially constant, for a given size of plant, and therefore the amount of compound applied by that means can be increased only by increasing the concentration of the dispersion. Depending on the circumstances, effective concentrations of compounds range from about 10 to about 1000 parts per million by weight. Factor which affect the effective amount include the succulence of the foliage, the rate at which it is growing, and the weather at the time of application. In general, preferred concentrations for foliar applications are in the range from about 50 to about 1000 parts per million by weight.

Measurement of the amount of compound applied as a dose per unit area of land may be used for either application to the soil or application to the foliage. Of course, it will be understood that application to the foliage results in some soil application in all cases, since not all of the composition applied to the foliage adheres there. In general, rates of from about 0.1 to about 10 pounds of compound per acre of crop land are useful. It is more preferred to use rates from about 0.5 to about 10 pounds per acre, most preferably, from about 0.5 to about 5 pounds per acre of the most preferred compounds.

It has been observed that application of the compound in multiple doses provides better effectiveness, and there is some indication that a smaller total amount of compound can effectively be used when applied in multiple doses. It may be that the result is explained by the fact that not all plants form anthers at the same time, and multiple applications avoid the necessity for compounds to be stored for a long period in the plant or soil. Application of a compound from 2 to 4 times, at intervals of 3 to 10 days, is preferred.

More particularly, application of a compound of the invention 2 or 3 times, where each application is of from about 0.125 to about 2 pounds of compound per acre, applied to the foliage, is particularly preferred. Further, application of the compound 2 or 3 times, where each application is of a dispersion containing from about 10 to about 250 parts per million by weight of compound, and the dispersion is applied so as to cover the foliage of the plants, is also preferred.

Another particularly preferred method of application of a compound of the invention is application to the soil in which the plants grow at a rate of from about 0.5 to about 5 pounds of compound per acre, applied once.

The plants to which a compound of the present invention may be applied to inhibit pollen formation are the cereal grain plants. A preferred group of species include wheat, barley, corn, rye and triticale. The more preferred species of plants are wheat and barley, and the most preferred species is wheat.

More particularly, the plants to which the invention is applied are defined as those which are sensitive to such treatment; that is, those in which the compounds will inhibit pollen formation when properly applied. The plants are defined in that manner because considerable variation in activity between varieties, and between individuals within a variety, has been observed. In barley, for example, some varieties require several times as much compound for activity as do other varieties.

In other species, of which corn is a particularly good example, the differences in sensitivity to the compounds are more subtle than varietal differences. It is therefore necessary, in such a species, to screen for sensitive plants, and to use the seed produced by those plants to create a variety of sensitive plants for further use in hybridization.

Of course, some experimentation is needed to use the present invention properly, particularly in species such as corn. The experimentation, however, is well understood and routinely carried out by plant breeders. The nature of the tests is clearly shown above in the test portion of this document, and so the skilled reader can readily plan routine experiments which will identify sensitive plants or varieties and determine the proper application rate of a compound, by the ordinary skills of the art, and the teaching in this document.

A further aspect of the present invention is the production of hybrid seed by use of the present pollen formation inhibiting method. Seed of the varieties which will be the male and female parents is planted in separate but adjacent plots. The female parent variety, of course, must be sensitive to the treatment of the present invention. The size and location of the plots may be important. Some species, such as wheat and barley, do not produce great quantities of pollen, as corn does, and so the pollen cannot be expected to travel very far and still fertilize a high percentage of the female plants. Therefore, the female plots should be relatively narrow. For example, the female and male parent seed may usefully be planted in long alternate plots, only a few rows wide, with their long axes oriented across the prevailing wind.

It has been observed to be advantageous to plant the female parent variety seed densely enough to inhibit the plants from developing tillers. The reason is that tillers develop later than the main plants, and therefore their presence confuses the determination of the proper time to apply the compound.

At the proper time, as discussed above in detail, the compound is applied to the female parent plots to inhibit those plants from producing pollen. Those plants are then pollinated by the male parent plants and produce hybrid seed, which is harvested in the usual ways.

The compositions in which a compound of the present invention may be formulated are of many types. Since the compounds are effective when applied both to the foliage of the plants, and to the soil in which the plants grow, substantially all of the physical types of agricultural chemical compositions may be used.

Most economical and preferred compositions are concentrated water-emulsifiable or water-dispersable compositions. Such compositions include, in general, emulsifiable concentrates, suspension concentrates and wettable powders and granules, all of which are common in the agricultural chemical art. Some discussion of them will be provided, however, to assure complete understanding.

The concentration of a compound in a concentrated composition is entirely irrelevant to the use of the compound. Such compositions are diluted in water for application, and the application rate of the compound is determined by the ratio at which the composition is diluted in water, or by the amount of the composition which is applied per area of crop land. Thus, any desired application rate can be obtained from any concentrated composition. Farmers and agricultural chemists are acquainted with the simple calculations which are necessary.

Emulsifiable concentrates of the compounds comprise a convenient concentration of the compound dissolved in a phytologically-acceptable diluent which is a mixture of water-immiscible organic solvent and emulsifiers. Useful organic solvents, in general, include aromatics, especially xylenes, and the petroleum fractions, especially the napthalenic and olefinic portions of petroleum, such as those called heavy aromatic naphthas. Terpenic solvents including rosin derivatives, and complex alcohols such as 2-ethoxy ethanol are also often used, and amides such as dimethylacetamide may be particularly useful with the present compounds. Suitable emulsifiers for emulsifiable concentrates, generally used in amounts in the range of from about 1% to about 10% by weight of the concentrate, are frequently found among the alkylbenzenesulfonates, the alkyl sulfates, the non-ionics such as ethylene oxide adducts of alkyl phenol, and especially among the metal and amine salts of alkyl sulfates.

Wettable powders comprise an intimate mixture of the compound and a phytologically-acceptable diluent made up of an inert carrier and surfactants. The inert carrier is usually chosen from among easily water-dispersable powdery substances such as attapulgite clay, the montmorillonite clays, the diatomaceous earths and the purified silicates. Surfactants for wettable powders are found among the same types just mentioned for emulsifiable concentrates, as well as the sulfonated lignins and the naphthalenesulfonates. It is possible to compact a wettable powder into granular form, and thereby to produce a wettable granule, which has the advantage of being non-dusty and easy to measure and pour. When added to water, a properly formulated wettable granular product will disperse and become a fine suspension.

The compounds may also be formulated as suspensions, which consist of a relatively high concentration, in the interest of economy, of the compound in finely powdered form, dispersed and suspended in a phytologically-acceptable aqueous diluent. A surfactant system for a suspension product is much like that used in a wettable powder, but it must be capable of maintaining the compound in dispersed form over a long period of time. It is sometimes advisable to adjust the density of the liquid, as by dissolving an inert salt in it, in order to assist in the suspension of the relatively dense particles of compound.

When an aqueous dispersion of a compound, prepared by the dilution of a concentrated composition, is to be applied to foliage, an adjuvant is often used to improve the ability of the dispersion to wet and adhere to the foliage. Such adjuvants as vegetable gums, emulsified polybutenes, cationic and other surfactants and lignin derivatives are often used. The use of an adjuvant in aqueous dispersions of the present compounds is highly preferred, and regularly improves results. Not only the commercial adjuvants, which are commonly known to growers, but also ordinary surfactants, are beneficially used, at concentrations in the range of a few tenths of a percent in the dispersion.

Aqueous dispersions of concentrated compositions may be applied either to foliage or to the soil in which plants grow. When the application is to be to the soil, a granular composition can also be effectively used. A granular agricultural composition consists of the compound, applied, usually in a relatively low concentration such as from about 1 to about 10% by weight, to a granular carrier having a convenient particle size for application. Typically, the particle size range is from 20 to 60 mesh, on the standard U.S. sieve size scale. Such carriers as clay, sand, pulverized stone, corncob grits and the like are frequently used and may be chosen for convenience and economy. It is usually unnecessary to use any adjuvant or other ingredient other than the compound and the carrier, with perhaps a small amount of solvent in which the compound is applied to the carrier. The carrier may also be supplied in powdered form, and formulated by mixing the powdered carrier with the powdered compound and then compacting the mixture and granulating it to the desired particle size range.

The following specific examples of formulations of compounds of the present invention are provided to assist the reader. It will be understood that the following formulations are merely exemplary of the manners of formulating the compounds. An agricultural chemist, using the following formulations as guides, can readily prepare any desired type of formulation, using any of the compounds of the invention as the active ingredient.

| Composition 1 | |
|---|---|
| 50% Wettable Powder | |
| compound of Example 1 | 51.6% |
| lignin sulfonate | 5.0 |
| precipitated silica | 5.0 |
| sodium alkylbenzene sulfonate | 5.0 |
| kaolin clay | 33.4 |

All of the ingredients were mixed, ground through a hammermill and finely ground in an air impact mill.

| Composition 2 | |
|---|---|
| 50% Wettable Powder | |
| compound of Example 2 | 51.6% |
| lignin sulfonate | 5.0 |
| precipitated silica | 5.0 |
| sodium alkylbenzene sulfonate | 5.0 |
| kaolin clay | 33.4 |

| Composition 3 | |
|---|---|
| 0.5% Granules | |
| compound of Example 1 | 0.52% |
| nonionic surfactant | 0.02 |
| white mineral oil | 0.18 |
| granular limestone | 99.28 |

The compound was finely ground, added to the limestone in a rotating drum, and the other ingredients were added as a fine spray.

| Composition 4 | |
|---|---|
| 0.5% Granules | |
| compound of Example 2 | 0.52% |
| nonionic surfactant | 0.02 |
| white mineral oil | 0.18 |
| granular limestone | 99.28 |

| Composition 5 | |
|---|---|
| 0.4% Granules | |
| compound | 0.4% |
| 30/60 mesh attapulgite | 99.6% |

| Composition 6 | |
|---|---|
| 1% Granules | |
| compound | 1.03% |
| 30/60 mesh attapulgite | 98.97% |

| Composition 7 | |
|---|---|
| 2% Granules | |
| compound | 2.06% |
| 30/60 mesh attapulgite | 97.94% |

| Composition 8 | |
|---|---|
| 4% Granules | |
| compound | 4.12% |
| 30/60 mesh attapulgite | 95.88% |

Composition 9

| 5% Granules | |
|---|---|
| compound | 5.15% |
| 30/60 mesh attapulgite | 94.85% |

Composition 10

| 10% Granules | |
|---|---|
| compound | 10.31% |
| 30/60 mesh attapulgite | 89.69% |

Composition 11

| 15% Granules | |
|---|---|
| compound | 15.46% |
| 30/60 mesh attapulgite | 84.54% |

All of compositions 1–11 are prepared by dissolving the compound in an appropriate amount of dimethylformamide and impregnating the carrier with the solution. The solvent is then evaporated, at high temperature if necessary.

Composition 12

| 1 lb./gal. Suspension | |
|---|---|
| compound | 12.1% |
| Pluronic P-104 (non-ionic surfactant) | 1.0% |
| silicone antifoam | 0.2% |
| propylene glycol | 6.0% |
| magnesium aluminum silicate | 1.0% |
| xanthan gum | 0.1% |
| water | 79.6% |

The compound is ground with the P-104, the antifoam and part of the water in an attrition mill for 45 minutes, and is then mixed with the rest of the ingredients.

Composition 13

| 25% Wettable Powder | |
|---|---|
| compound | 26.9% |
| sodium salt of lignin with anionic wetting agents | 10.0% |
| purified silica | 10.0% |
| kaolin clay | 53.1% |

The above ingredients are thoroughly mixed, and the mixture is then milled through a hammermill and then through an air impact mill.

Composition 14

| 0.5 lb./gal. Suspension | |
|---|---|
| compound | 6.2% |
| Tergitol TMN-6 (non-ionic surfactant) | 5.0% |
| purified silica | 0.5% |
| silicone antifoam | 0.1% |
| 2% xanthan gum | 5.0% |
| water | 83.2% |

The compound is ground with part of the water, the silica and the antifoam in an attrition mill until 50% of the particles are smaller than 1 micron by microscopic inspection, and the suspension is then mixed with the rest of the ingredients.

Composition 15

| 1 lb./gal. Suspension | |
|---|---|
| compound | 12.1% |
| Tergitol TMN-6 | 1.0% |
| Polyfon H (lignin sulfonate salt) | 2.0% |
| 5% magnesium aluminum silicate suspension | 20.0% |
| 2% xanthan gum suspension | 5.0% |
| silicone antifoam | 0.2% |
| water | 59.7% |

The compound is ground in an attrition mill with the Tergitol, the Polyfon and part of the water, and is then mixed with the rest of the ingredients.

Composition 16

| 1 lb./gal. Suspension | |
|---|---|
| compound | 12.1% |
| Tergitol TMN-6 | 1.0% |
| Polyfon H | 2.0% |
| 5% magnesium aluminum silicate suspension | 20.0% |
| 2% xanthan gum suspension | 5.0% |
| propylene glycol | 6.0% |
| silicone antifoam | 0.2% |
| water | 53.7% |

The compound is ground in an attrition mill with the Tergitol, the Polyfon and part of the water, and is then mixed with the rest of the ingredients.

Composition 17

| 1 lb./gal. Suspension | |
|---|---|
| compound | 12.1% |
| Makon 12 (non-ionic surfactant) | 1.0% |
| 5% magnesium aluminum silicate suspension | 20.0% |
| 2% xanthan gum suspension | 5.0% |
| silicone antifoam | 0.2% |
| water | 61.7% |

The compound is ground in an attrition mill with the Makon, the antifoam and part of the water and is then mixed with the rest of the ingredients.

Composition 18

| 1 lb./gal. Suspension | |
|---|---|
| compound | 12.1% |
| Makon 12 | 1.0% |
| propylene glycol | 6.0% |
| 5% magnesium aluminum silicate suspension | 20.0% |
| 2% xanthan gum suspension | 5.0% |
| silicone antifoam | 0.2% |
| water | 55.7% |

The compound is ground in an attrition mill with the Makon, the antifoam and part of the water, and is then mixed with the rest of the ingredients.

Composition 19

| 1 lb./gal. Suspension | |
|---|---|
| compound | 12.1% |
| Pluronic P-104 | 1.0% |
| 5% magnesium aluminum silicate suspension | 20.0% |
| 2% xanthan gum suspension | 5.0% |

| Composition 19 1 lb./gal. Suspension | |
|---|---|
| silicone antifoam | 0.2% |
| water | 61.7% |

The compound is ground in an attrition mill with the Pluronic, the antifoam and part of the water, and is then mixed with the rest of the ingredients.

| Composition 20 5% Suspension | |
|---|---|
| compound | 5.0% |
| sodium napthaleneformaldehyde condensate | 3.0% |
| 30% formaldehyde | 0.4% |
| xanthan gum | 0.4% |
| propylene glycol | 5.0% |
| water | 86.2% |

The mixture is ground until the average particle size is 3 microns.

| Composition 21 5% Granules | |
|---|---|
| compound | 5.0% |
| sand | 95.0% |

The compound is dissolved in N-methylpyrrolidone, the appropriate amount of the solution is mixed with the carrier, and the solvent is evaporated.

We claim:

1. A method of producing hybrid cereal grain seed having a male and a female parent variety, comprising planting seed of said male and female parent varieties in separate plots adjacent to each other, supplying to the female parent plants growing from said female parent seed, at a time prior to anther formation, a pollen formation inhibiting amount of a compound of the formula

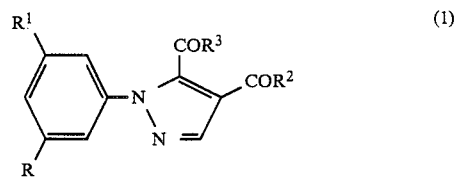

wherein
R and $R^1$ independently represent chloro, bromo, or methyl;
$R^2$ is hydroxy, $C_1$–$C_4$ alkoxy, $C_3$–$C_4$ alkenoxy, $C_3$–$C_4$ alkoynoxy, or a phytologically-acceptable moiety forming a salt of the carboxylic acid;
$R^3$ is $NH_2$, hydroxy, or a phytologically-acceptable moiety forming a salt of the carboxylic acid;
or $R^2$ and $R^3$ combine to form an imide;
provided that $R^3$ is $NH_2$ when $R^2$ is alkoxy, alkenoxy, or alkynoxy; and that $R^2$ and $R^3$ are the same when $R^3$ is other than $NH_2$; said female parent variety being sensitive to said treatment, allowing said treated female parent plants to be pollinated by the male parent plants growing from said male parent seed and to produce hybrid seed, and harvesting said hybrid seed from the treated female parent plants.

2. The method of claim 1 wherein the compound of formula (1) is 4-carboxy-1-(3,5-dichlorophenyl)-5-pyrazolecarboxamide or a phytologically-acceptable salt thereof.

3. The method of claim 1 wherein the compound of formula (1) is 4-carboxy-1-(3,5-dimethylphenyl)-5-pyrazolecarboxamide or a phytologically-acceptable salt thereof.

* * * * *